(12) United States Patent  (10) Patent No.: US 8,377,134 B2
Khandkar et al.  (45) Date of Patent: *Feb. 19, 2013

(54) TOTAL DISC IMPLANT

(75) Inventors: Ashok C. Khandkar, Salt Lake City, UT (US); Darrel S. Brodke, Salt Lake City, UT (US); Ramaswamy Lakshminarayanan, Salt Lake City, UT (US)

(73) Assignee: Amedica Corporation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/136,886

(22) Filed: Aug. 11, 2011

(65) Prior Publication Data

US 2012/0123545 A1  May 17, 2012

Related U.S. Application Data

(60) Continuation of application No. 12/803,889, filed on Jul. 7, 2010, now Pat. No. 8,016,890, which is a continuation of application No. 11/858,016, filed on Sep. 19, 2007, now Pat. No. 7,771,481, which is a division of application No. 11/149,627, filed on Jun. 9, 2005, now Pat. No. 7,758,646, which is a division of application No. 10/737,108, filed on Dec. 15, 2003, now Pat. No. 6,994,727.

(60) Provisional application No. 60/434,092, filed on Dec. 17, 2002.

(51) Int. Cl.
*A61F 2/44* (2006.01)
(52) U.S. Cl. .................................. 623/17.15; 623/17.14
(58) Field of Classification Search .................... None
See application file for complete search history.

*Primary Examiner* — David H Willse
*Assistant Examiner* — Javier Blanco
(74) *Attorney, Agent, or Firm* — Mintz Levin Cohn Ferris Glovsky and Popeo, P.C.

(57) ABSTRACT

A total disc implant (TDI) is provided for total replacement of a spinal disc or discs in a human patient or other mammal, wherein the TDI is designed to maintain a substantially full range of natural motion (ROM) following implantation. The TDI generally comprises, in one preferred form, upper and lower end plates for affixation to adjacent vertebral bodies, with an intervening insert disposed therebetween. The end plates each include elongated part-cylindrical surfaces oriented, generally perpendicular to each other, with one of the surfaces extending in an anterior-posterior direction and the other extending in a medial-lateral direction. The intervening insert defines concave upper and lower part-cylindrical seats oriented, for respectively engaging these part-cylindrical surfaces, wherein these part-cylindrical seats are defined by offset radii to include a somewhat flattened central base region merging smoothly with upwardly curving radiused sides.

4 Claims, 7 Drawing Sheets

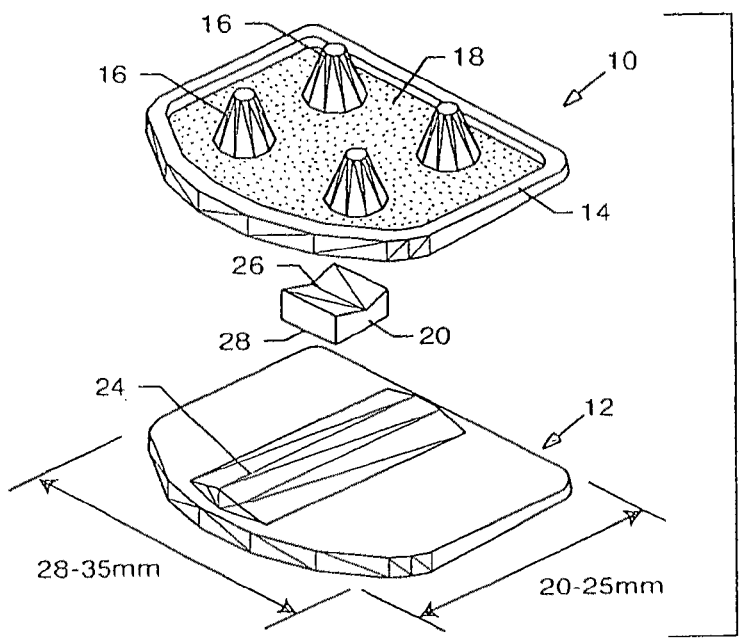
FIG. 1
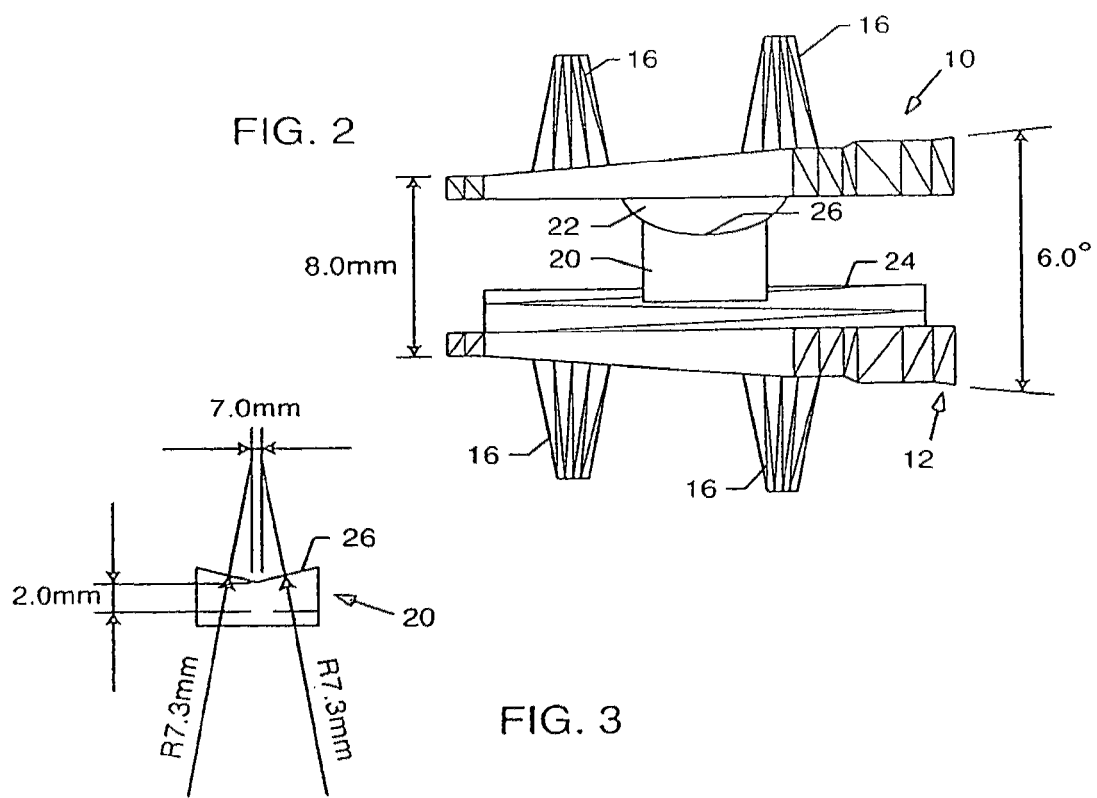
FIG. 2
FIG. 3

TOTAL DISC IMPLANT

This application is a continuation of U.S. Ser. No. 12/803,889, filed Jul. 7, 2010, now U.S. Pat. No. 8,016,890, which is a continuation of U.S. Ser. No. 11/858,016, filed Sep. 19, 2007, now U.S. Pat. No. 7,771,481, which is a division of U.S. Ser. No. 11/149,627, filed Jun. 9, 2005, now U.S. Pat. No. 7,758,646, which is a division of U.S. Ser. No. 10/737,108, filed Dec. 15, 2003, now U.S. Pat. No. 6,994,727, which in turn, claims the benefit of U.S. Provisional Application 60/434,092, filed Dec. 17, 2002. The contents of each are hereby incorporated by reference herein in their entireties.

BACKGROUND OF THE INVENTION

This application claims the benefit of U.S. Provisional Application 60/434,092, filed Dec. 17, 2002.

A novel motion preserving total disc replacement implant (TDI) is provided. The TDI is particularly designed for implantation into a human patient or other mammal, into the inter-vertebral space between adjacent spinal discs or vertebrae, as a prosthetic replacement for one or more surgically removed discs. The TDI beneficially provides a substantially full and natural post-operative range of motion (ROM).

In the preferred form, the components of the TDI of the present invention are formed from ceramic materials, or biocompatible metals, or a combination thereof, with preferred ultra-low wear ceramic-ceramic or ceramic-metal articulatory components and materials being described in copending U.S. Ser. No. 10/171,376. filed Jun. 13, 2002, and entitled METAL-CERAMIC COMPOSITE ARTICULATION, which is incorporated by reference herein. Such ultra-low wear bearing material or materials have shown impressive mechanical and tribological properties for hip articulations, and may be used in the TDI of the present invention thereby avoiding the problems and disadvantages associated with prior art concepts using metal end plates articulating with a conventional high molecular weight polyethylene (PE) insert.

Spinal disc herniation and the often resultant symptoms of intractable pain, weakness, sensory loss, incontinence and progressive arthritis are among the most common debilitating conditions affecting mankind. If a patient's condition does not improve after conservative treatment, and if clear physical evidence of nerve root or spinal cord compression is apparent, and if correlating radiographic studies (i.e., magnetic resonance imaging (MRI) or X-ray computer tomography (CT) imaging or myelography) confirm the condition, discectomy, or surgical removal of the affected disc is often resorted to. In the United States in 1985, over 250,000 such operations were performed in the lumbar spine and cervical spine.

Statistics suggest that present surgical techniques are likely to result in short-term relief, but do not prevent the progressive deterioration of the patient's condition in the long run. Through better pre-operative procedures and diagnostic studies, long-term patient results have improved somewhat. But it has become clear that unless the removed disc is replaced or the spine is otherwise properly supported, further degeneration of the patient's condition will almost certainly occur.

In the mid-1950's and 60's, Cloward and Smith & Robinson popularized anterior surgical approaches to the cervical spine for the treatment of cervical degenerative disc disease and related disorders of the vertebrae, spinal cord and nerve root; these surgeries involved disc removal followed by interbody fusion with a bone graft. It was noted by Robinson[i] that after surgical fusion, osteophyte (bone spur) re-absorption at the fused segment might take place. However, it has become increasingly apparent that unfused vertebral segments at the levels above and below the fused segment degenerate at accelerated rates as a direct result of this fusion. This has led some surgeons to perform discectomy atone, without fusion, by a posterior approach in the neck of some patients. However, as has occurred in surgeries involving the lower back where discectomy without fusion is more common as the initial treatment for disc herniation syndromes, progressive degeneration at the level of disc excision is the rule rather than the exception.

Similarly, in addition to the problems created by disc herniation, traumatic, malignant, infectious and degenerative syndromes of the spine also involve fusion of spine segments. Other procedures include bone grafts and metallic rods, hooks, plates and screws being appended to the patient's anatomy; often they are rigidly and internally fixed. None provide for a patient's return to near-normal functioning. Though these procedures may address the symptoms in the short-term; they can result in progressive degeneration of discs at adjacent levels in the longer term. This is due to the adjacent discs attempting to compensate for the lack of motion of the fused segment. In fact, it is now well recognized that premature degenerative disc disease at the level above and below the excised disc can and does occur. Hence, motion preserving total disc replacements are a promising alternative to spine fusion devices. This next generation of spinal implants in fact, mirror the progression in other articulating joints such as hips and knees: from arthrodesis to arthroplasty.

While long term clinical data are unavailable, the current generation of articulating disc implants typically have metal end plates with a compliant articulating, typically high density polyethylene (PE) insert between them. Compliant inserts are used to enable low friction articulation and also to enable resilient cushioning under load, although no clinical proof exists that shock absorption is necessary. The long history of similar metal/PE articulations for hip and knee protheses indicates that in the long term, PE wear particles are one of the principal causes of implant failures. In hip implants for example, the ultra-high molecular weight polyethylene (PE) particles are released over time from the acetabular[ii, iii, iv]. This wear debris is released into the peri-implant tissue and elicits a deleterious biologic reaction, incorporating foreign-body giant cell and macrophage cell responses leading to bone resorption, and eventual implant failure. As a consequence, alternate rigid-on-rigid bearing materials such as alumina-on-alumina ceramic, metal-on-metal, and the recent cobalt-chromium (CoCr) alloy—heavily cross-linked PE have been introduced.

It is instructive to follow the evolution of knee joint implants since they are kinematically analogous to intervertebral discs: they have a similar range of complex motion including sliding in the anterior-posterior (A-P) direction, rotation and bending in the medial-lateral (M-L) direction, and combinations thereof. Early designs had unacceptable failures due to aseptic loosening resulting from poor conformity leading to instability, high contact stresses, and high PE insert wear. Despite lower loads on the knee joint, backside wear of the PE tibial insert resulting from sliding motion was a major cause for concern[v]. Implant stability was found to be a function of how well the tibial component was fixed. Extensive retrieval analysis of knee implants has indicated that proper fit, fixation and initial stability of the tibial component was critical to achieving clinical success. Stated alternatively, development of an appropriate ingrowth surface to achieve consistent bony fixation over large cancellous regions was critical to implant success[vi, vii]. More recent knee implant designs have included mobile bearing platforms that allow rotation and A-P translation. The articulations have improved conformity and kinematics, which lead to reduced contact stresses. However new problems arise: bearings without stops can dislocate or spin-out, and bearings with stops can wear as they abut against the mechanical stops that prevent dislocation.[viii]

Diagnostic imaging using radiography or MRI is commonly used to assess the presence of spinal disease, determine range of motion or evaluate the patients progress in healing post surgical treatment[ix, x]. The present generation of total disc replacements use metal end plates which present problems with imaging MRI or in X-Ray -CT imaging, due to the presence of halos and other artifacts.

Finally, an important requirement for total disc implants is that the articulating disc does not protrude or impinge on the spinal cord or nerve roots, which is a concern with compliant materials.[xi] As has been well established from other articulating joints such as the knee, PE inserts can suffer damage from several modes: creep, pitting, scratching, burnishing, abrasion, delamination and embedded particulates. While there is debate over whether creep or wear is the main cause of dimensional changes in PE inserts[xii, xiii], there is little doubt that damage to PE can and does occur over the long term.

Thus, there is a need to develop an alternative to the present generation of disc implants, typically with respect to those designed from metal/PE articulations, and to overcome a number of potential drawbacks:
 [a] Long term wear of the articulating PE "disc", especially in cases where small bony fragments are entrapped between the articulating surfaces,
 [b] Osteolysis and subsequent aseptic loosening and instability of the implant as a result of the PE wear debris,
 [c] Protrusion of the disc from the disc space due to creep or fatigue related gradual changes in dimensional characteristics, and
 [d] Difficulty of diagnostic imaging the intervertebral region because of electromagnetic artifacts, halos and radiographic shadows associated with the metal end plates.

The proposed TDI design of the present invention is geometrically configured to accommodate a substantially full and natural range of motion, and, in the preferred form, is constructed from an alternate ultra-low wear bearing material that restores anatomic function avoids all the drawbacks of current artificial disc designs.

SUMMARY OF THE INVENTION

In accordance with the invention, a total disc implant (TDI) is provided for total replacement of a spinal disc or discs in a human patient or other mammal, wherein the TDI is designed to maintain a substantially full range of natural motion (ROM) following implantation. In generally, the TDI comprises upper and lower end plates for affixation to adjacent vertebral bodies, wherein this pair of end plates are adapted for accommodating a substantially full and natural range of anterior-posterior (A-P) rotation or flexion, medial-lateral (M-L) rotation or flexion, and axial rotation.

In one preferred form, the TDI generally comprises the upper and lower end plates for affixation to adjacent vertebral bodies, in combination with an intervening insert disposed therebetween. The upper and lower end plates Include elongated and generally convex part-cylindrical surfaces oriented generally perpendicular to each other, with one of said surfaces extending in an anterior-posterior direction and other extending in a medial-lateral direction. The intervening insert defines concave upper and lower part-cylindrical seats oriented generally perpendicular to each other for respectively engaging these part-cylindrical surfaces, but wherein at least one and preferably both of these part-cylindrical seats are defined by offset radii to include a somewhat flattened central base region merging smoothly with upwardly curving radiused sides. With this geometry, the TDI accommodates a substantially full and natural range of motion, including anterior-posterior flexion, medial-lateral extension, and a limited range of axial rotation.

In an alternative form, an elongated and generally convex part-cylindrical surface is formed on one of the upper and lower end plates, and a generally convex part-cylindrical seat defined preferably by offset radii is formed on the other of the two end plates. When the upper and lower end plates are suitably affixed to adjacent vertebral bodies, the part-cylindrical convex surface is retained in articulating engagement with the part-cylindrical concave seat, in a manner permitting a substantially full and natural range of motion, including anterior-posterior flexion, medial-lateral extension, and a limited range of axial rotation.

Preferred materials include ceramic, with a most preferred material being sintered silicon nitride ($Si_3N_4$), for the upper and lower end plates and insert, or a biocompatible metal such as titanium or cobalt-chrome alloy, or a combination of such ceramic and metal materials. Preferred ceramic materials for use in a ceramic-ceramic or a ceramic-metal articulation interface are disclosed in copending U.S. Ser. No. 10/171, 376, filed Jun. 13, 2002, which is incorporated by reference herein.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an exploded top perspective view showing a total disc implant constructed in accordance with one preferred form of the present invention, and illustrating upper and lower end plates with an insert positioned therebetween;

FIG. 2 is a side elevation view of the total disc implant depicted in FIG. 1;

FIG. 3 is an enlarged side elevation view of the insert;

DETAILED DESCRIPTION OF THE PREFERRED EMBODIMENTS

Figure 4:
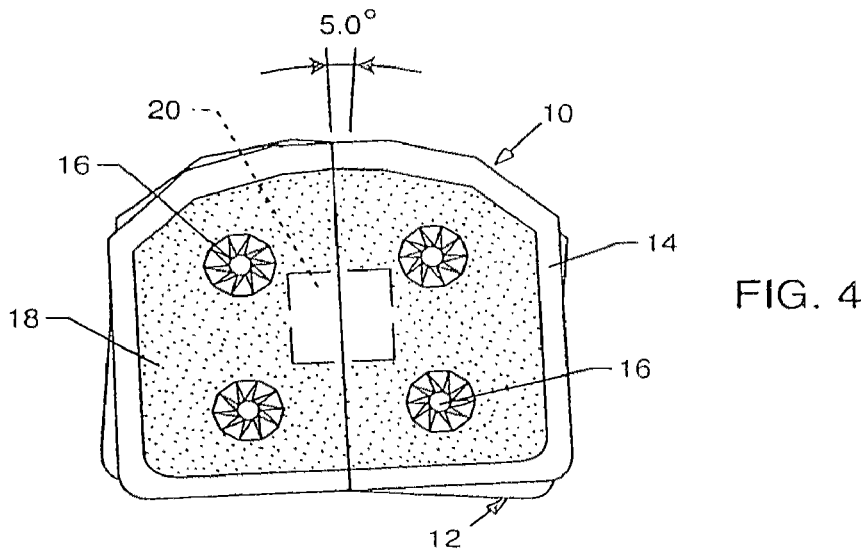
FIG. 4 is a top plan view of the total disc implant of FIG. 1, showing axial rotation.

The TDI design of the present invention is based on the principles of maintaining spine anatomy, restoring function by preserving segmental motion, providing immediate stability, withstanding spine loads safely, and providing rapid osteo-integration between implant/host bone.

FIGS. 1 and 2 show the proposed TDI design for lumbar spine. The design features an upper end plate 10 and a lower end plate 12 formed respectively with upper and lower surfaces that engage with the adjacent vertebral bodies (not shown). Each end plate 10, 12 includes a solid rim 14 substantially circumscribing the respective upper and lower surface to rest on the cortex of the adjacent vertebral body. Fixation elements such as fins, teeth or pins 16 protrude axially from the respective upper and lower surfaces of the end plates 10, 12 to provide anchoring and immediate stability with the adjacent vertebral bodies. These upper and lower surfaces include or are surface-coated each to define a porous in-growth surface 18 to permit and accommodate rapid bone in-growth and osteo-integration for long term stability. A variety of suitable bone ingrowth coatings and materials are known to persons skilled in the art. In addition, while these in-growth surfaces are depicted with a generally planar configuration in FIGS. 1 and 2, alternative geometries particularly, such as a convexly contoured or domed configuration for more optimal and extended surface area contact with adjacent porous or cancellous interior structures of prepared adjacent vertebral bodies, will be apparent to persons skilled in the art.

The anterior-posterior (A-P) and medial-lateral (M-L) dimensions of the upper and lower end plates 10, 12 are chosen to suit typical lumbar/cervical spinal body dimensions, such as an A-P dimension of about 20-25 mm and a M-L dimension of about 28-35 mm as viewed in the illustrative drawings. The illustrative end plates 10, 12 further include an anterior to posterior lordotic taper to better restore the natural curvature of spine, as viewed in FIG. 2 which shows each end plate 10, 12 with a tapered thickness that increases in the anterior to posterior direction. As viewed in FIG. 2, upon assembly of the total disc implant (as will be described in more detail), this lordotic taper may provide a posterior spacing between the end plates 10, 12 of about 8 mm, with the upper and lower surfaces of the end plates 10, 12 tapering forwardly in the anterior direction at a diverging angle of about 6 degrees.

The articulating lower surface of the upper end plate 10, and the articulating upper surface of the lower end plate 12 each include a unique contour that permits a substantially normal range flexion in the A-P direction in combination with extension in the M-L direction, while additionally accommodating a limited range of axial rotation. These articulating surfaces of the upper and lower end plates 10, 12 respectively engage and articulate with an intervening insert 20 having uniquely contoured upper and lower surfaces.

More particularly, the articulating lower surface of the upper end plate 10 comprises a part-cylindrical, downwardly convex elongated bearing component or strip 22 defining a bearing surface extending generally in the M-L direction. The articulating upper surface of the lower end plate 12 comprises a similarly sized and shaped, part-cylindrical and upwardly convex elongated bearing component or strip 24 oriented to define a bearing surface extending generally in the A-P direction. Thus, the two bearing strips 22, 24 are oriented generally on orthogonal axes relative to each other.

The insert 20 is captured between these bearing strips 22, 24, and includes generally part-cylindrical recessed bearing seats 26 and 28 formed respective in the upper and lower sides thereof, generally on mutually orthogonal axis, for respective reception and bearing engagement with the part-cylindrical bearing strips 22, 24. Accordingly, the articulating geometry between the upper bearing strip 22 on the upper end plate 10, with the upper bearing seat 26 on the insert 20, accommodates A-P rotation or flexion (as viewed in FIG. 5), with a preferred range of A-P flexion on the order of about 12-15°. In a similar manner, the articulating geometry between the lower bearing strip 24 on the lower end plate 12, with the lower bearing seat 28 on the insert 20, accommodates M-L rotation or extension (as viewed in FIG. 6), with a preferred range of M-L extension on the order of about 12-15° of lateral bending. While the illustrative drawings depict a relatively small insert 20 (in plan view, relative to the size of the end plates 10, 12, persons skilled in the art will recognize and appreciate that the outer dimensions of the insert 20 can be selected and varied as desired to suit a specific patient, and/or to reduce or eliminate the risk of insert dislocation or expulsion from between the end plates 10, 12 during normal patient movement.

In accordance with one primary aspect of the invention, the recessed part-cylindrical bearing seats 26,28 formed on the insert 20 each have a part-cylindrical contour defined in cross sectional shape by offset radii, as shown best in FIG. 3. In particular, each bearing seat 26, 28 is defined by upwardly curving sides shown in the illustrative example of FIG. 3 to be formed on radii of about 7.3 mm, but wherein the centers of these radii are spaced apart or laterally offset by a small increment (0.7 mm in the illustrative example) to provide a relatively flattened base segment interposed between the upwardly curving radiuses sides.

With this geometry, the part-cylindrical bearing seats 26, 28, defined by offset radii, provide a platform permitting a limited amount of axial rotation and translation. That is, the effect of this special asymmetric articulating geometry with offset radii is to accommodate a substantially natural range of anatomic rotational motion on the order of about plus/minus 5° as viewed in FIG. 4, while at the same time providing a limit to extreme rotation motion and restoring a "neutral" position following a rotation motion. In such rotation, the radiused sides of the insert 20 initially abut the bearing strips 22, 24 of the top and bottom plates 10, 12 (FIG. 4). Further rotation results in the insert 20 sliding along the articulating bearing strips 22, 24 of the top and bottom end plates 10, 12 effectively distracting the intervertebral disc space. This distraction increases loading on the TDI. In turn, the increased loading naturally results in a counteracting force tending to resist the distraction, forcing the two vertebral bodies back to the "neutral" position.

Thus, this unique TDI articulation geometry functions like the natural disc, by limiting axial rotation while permitting normal anatomic flexion-extension and lateral bending motions. No other features such as positive stops or grooves or additional components such as elastomeric materials are necessary.

Figure 5:
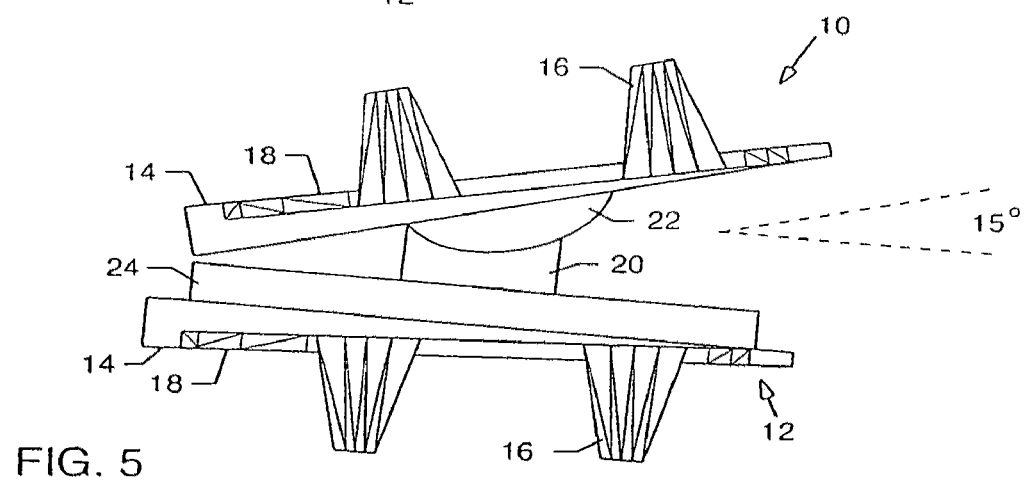
FIG. 5 is an anterior-posterior or sagital sectional view of the total disc implant of FIG. 1, showing anterior-posterior articulation.
Figure 6:
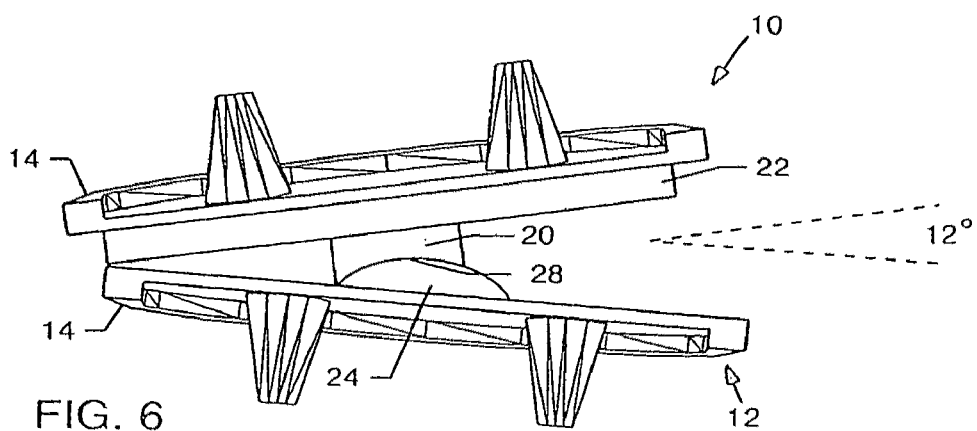
FIG. 6 is a medial-lateral or coronal sectional view of the total disc implant of FIG. 1, showing medial-lateral articulation.

FIGS. 5 and 6 show the implant design in the extreme lateral bending and flexion-extension positions respectively. As can be noted, anatomic combined lateral bending and flexion-extension range of motion (ROM) are permitted for the lumbar implant. The total intervertebral height is in the illustrative embodiment is about 8 mm. For the cervical implant, the design permits a higher range of motion—up to about 20° for flexion-extension and lateral bending. The ROM for the proposed lumbar and cervical spines are in accord with those reported by Wilke et al[xiv, xv] and White and Panjabi[xvi].

The significant clinical advantages of the design are:
1. Universal Design for Lumbar and Cervical Applications: the design, as shown, is suited for a lumbar implant. Suitable modifications of its dimensions permits its use as a cervical disc implant. The objective is to offer a range of sizes that fit the spine in any intervertebral disc space, and without alteration of that inter-vertebral space regardless of its natural size or shape.
2. Restoration and Preservation of Anatomic Motion: the objective of the total disc implant (TDI) is to restore intervertebral space to its natural pre-morbid dimensions and provide full range of motion including limiting extreme motion just like in normal spines. A further goal is to prevent adjacent segment hypermobility. The proposed TDI is more natural—allowing controlled and limited motion between segments. In contrast to some current designs, the TDI has a special bi-convex articulating contour or geometry which permits "normal" flexion-extension, lateral bending, and limited axial rotation. This geometry is in sharp contrast to some designs which use fixed hard stops (e.g.,. Flexicore), with the potential for implant loosening, or other discs such as the Charite', ProDisc and Maverick which have passive stops to limit axial rotation, and require the annulus to be tightened for optimal function.
3. Minimal End Plate Preparation: by preserving the load bearing cortical bone and minimizing end plate perforation to expose the highly vascular cancellous bone, both immediate stability and long term in-growth is enabled.
4. Surgical Technique: the surgical technique for insertion of these implants is consistent with the established methods of disc removal, and requires neither specialized instrumentation nor specialized instrumentation nor specialized surgical technique. In fact, the technique will be similar to that used for over a decade for artificial discs. The technique involves removal of the nucleus pulposus, flattening of the end plates and leaving most of the annular circumferentially intact. The anterior or anterior-lateral aspect of the annulus is removed as needed for TDI placement. Based upon templating the patient spine and using trial implants, the vertebral bodies are distracted to a near maximum needed for optimal placement of the TDI. The fins cut through the end plates and the osteo-integration surface, which may be domed, is forced into contact with the cancellous portion of the adjacent vertebral bodies. Ligamentoxasis is also used to maintain the TDI in place. The surgical goal is to relieve pain by restoring the patient's natural spinal anatomy and allowing for some motion between the diseased vertebral segments, and thereby minimize or avoid adjacent segment hypermobility. Clinical success will be defines by reduction or elimination of patient pain, improvement in function and maintenance of motion with the TDI.
5. Extent of Disc Removal: the extent of disc removal can be determined by the surgeon at the time of surgery and can be individualized for each patient. As noted above, the end plate is flattened most of the annulus is left circumferentially intact. It is contemplated that multiple TDI's with variable height end plates insert will be provided in order to restore a unique individual anatomy with a relatively high degree of precision.
6. Elimination of Incorrect Implant Size Selection: in those implant systems where a drill is used and significant bone is removed, trials of the implant size must first be made. Furthermore, regardless of the fit, an implant at least as large as the space created by the drilling must be utilized, regardless of the quality of that fit. With the proposed design, no significant bone is removed, and the correct size implants are fitted directly to the inter-vertebral space eliminating the need to guess at the correct implant size before the fact. At the surgeon's discretion and based on the templating of the patient's spine, the surgeon will choose the appropriate implant size in order to restore the patient's spinal anatomy.
7. Modular Design: the proposed implant design will be made available in different standardized A-P depths and M-L widths to accommodate the physiological range of inter-vertebral space. The articulating inserts will also be made available in varying heights within typical the physiological range. This will enable standardization of the modular implant system over the lumbar/cervical size ranges.
8. Avoidance of Collapse of the Inter-vertebral space: the implant is made from ceramic material many times stronger than bone and will not collapse. The implantation technique and TDI design relies on preservation of the strong vertebral cortex, which is resistant to compression, thus preventing or minimizing migration or subsidence of the TDI into the vertebrae. The large bearing surface area of the implant minimizes the load per unit area on the insert.
9. Revisability: the proposed TDI is an inter-vertebral space implant and not a "through vertebrae" cross inter-vertebral space implant. The technique envisioned requires minimal end plate preparation. Furthermore, the design features multiple 2 mm fins which bite into the adjacent vertebral bone for stability. It is expected that revision of the implant, should it become necessary, would be possible with a minimal chance of iatrogenic destruction of the adjacent vertebrae.
10. Self-Stabilizing with Rapid Osteo-integration Capability: the implant surface is designed to resist dislodgment with multiple fins assuring immediate anchoring. Long term stability is provided by rapid osteo-integration into the bio-mimetic cancellous structured bony ingrowth layer. Loading the porous layer with osteo-inductive agents can enhance this ingrowth.

11. Safety and Versatility: the entire procedure is performed under direct vision and with complete visualization of the adjacent vital structures (e.g., organs, neural structures and blood vessels). The implant also lends itself to a variety of implantation techniques such as minimally invasive surgery, anterior, posterior, lateral or extreme lateral approaches.

Figure 7:
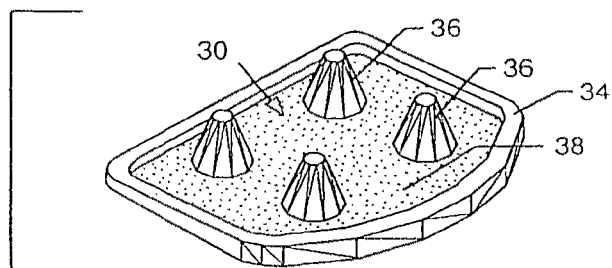
FIG. 7 is an exploded top perspective view showing a total disc implant constructed in accordance with an alternative preferred form of the present invention.
Figure 8:
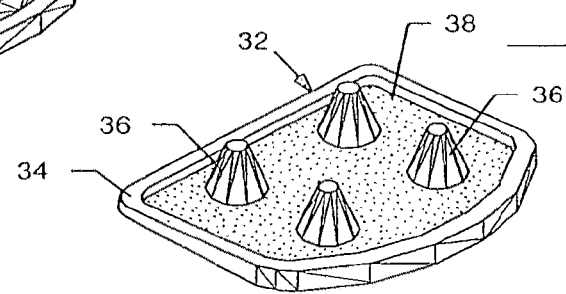
FIG. 8 is an exploded bottom perspective view of the total disc implant of FIG. 7.
Figure 9:
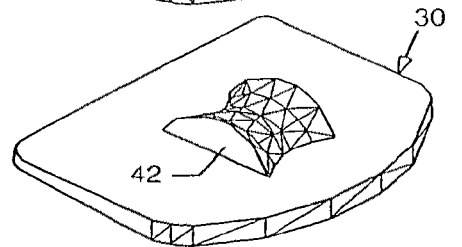
FIG. 9 is a side elevation view of the total disc implant depicted in FIG. 7.
Figure 9:
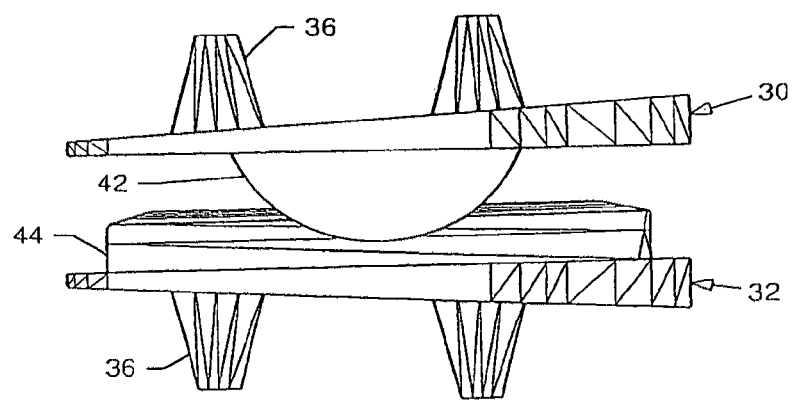

FIGS. 7-9 show an alternate TDI design for lumbar spine. The design features an upper end plate 30 and a lower end plate 32 formed respectively with upper and lower surfaces that engage with the adjacent vertebral bodies (not shown). Each end plate 30, 32 includes a solid rim 34 substantially circumscribing the respective upper and lower surface to rest on the cortex of the adjacent vertebral body. Fixation elements such as fins, teeth or pins 36 protrude axially from the respective upper and lower surfaces of the end plates 30, 32 to provide anchoring and immediate stability with the adjacent vertebral bodies. These upper and lower surfaces include or are surface-coated each to define a porous in-growth surface 38 to permit and accommodate rapid bone in-growth and osteo-integration for long term stability. A variety of suitable bone ingrowth coatings and materials are known to persons skilled in the art. Once again, while illustrative drawings show the in-growth surface 38 to have a generally planar shape, persons skilled in the art will understand that alternative configurations such as a convexly or similarly extended surface area contour may be preferred.

The A-P and M-L dimensions of the upper and lower end plates 30, 32 are chosen to suit typical lumbar/cervical spinal body dimensions. The illustrative end plates 30, 32 further include an anterior to posterior lordotic taper to better restore the natural curvature of spine, as viewed in FIG. 9.

The articulating lower surface of the upper end plate 30, and the articulating upper surface of the lower end plate 32 each include a unique bearing component defining a unique bearing surface or contour that permits a substantially normal range flexion in the A-P direction in combination with extension in the M-L direction, while additional accommodating a limited range of axial rotation. These articulating surfaces of the upper and lower end plates 30, 32 respectively engage and articulate with each other.

More particularly, the articulating surface of the upper end plate 30 comprises a part-cylindrical, downwardly concave bearing component or member 42 with its axis extending generally perpendicular to the M-L direction. The articulating surface of the lower end plate 32 comprises a similarly sized and shaped, part-cylindrical and upwardly convex elongated bearing component. or strip 44 oriented to extend generally in the A-P direction. Thus, the two bearing surfaces 42, 44 are oriented generally on orthogonal axes relative to each other.

Figure 10:
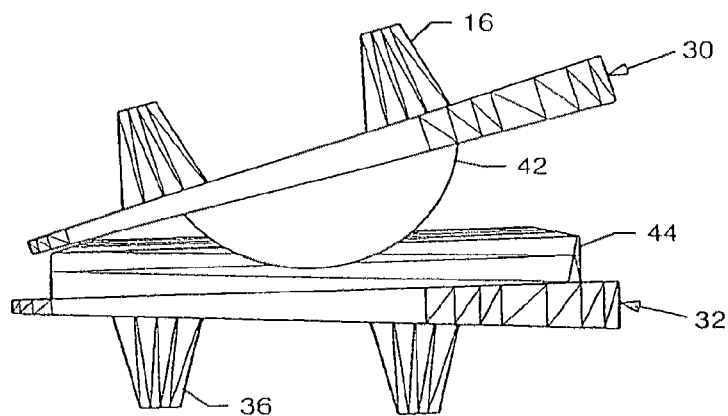
FIG. 10 is an anterior-posterior or sagital sectional view of the total disc implant of FIG. 7, showing anterior-posterior articulation.
Figure 11:
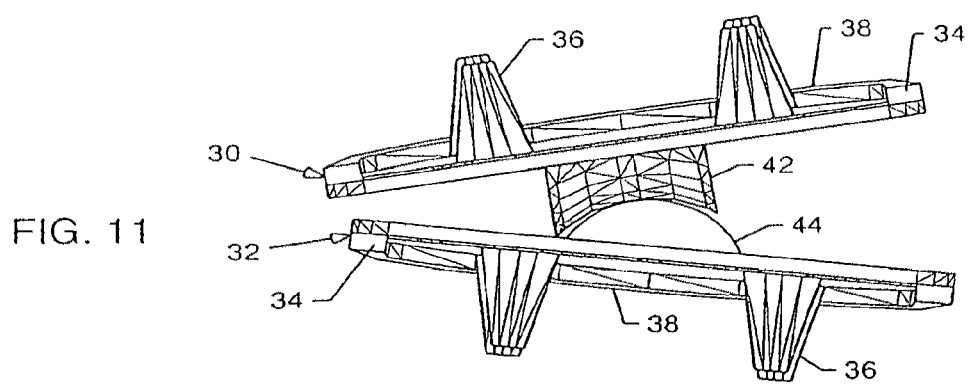
FIG. 11 is a medial-lateral or coronal sectional view of the total disc implant of FIG. 7, showing medial-lateral articulation.

Accordingly, the articulating geometry between the upper bearing surface 42 on the upper end plate 30, accommodates A-P rotation or flexion (as viewed in FIG. 10), with a preferred range of A-P flexion on the order of about 12-15°. In a similar manner, the articulating geometry between the lower bearing strip 44 on the lower end plate 30, accommodates M-L rotation or extension (as viewed in FIG. 11), with a preferred range of M-L extension on the order of about 12-15° of lateral bending.

In accordance with one primary aspect of the invention, the part-cylindrical bearing surfaces 42, 44 formed on the upper and lower end plates 30 and 32 each have a part-cylindrical contour defined by offset radii, similar to those shown best in FIG. 3. In particular, each bearing surface 42, 44 is defined by curving sides to be formed as arcs of a circle, but wherein the centers of these arcs are spaced apart or laterally offset by a small increment to provide a relatively flattened rotational platform interposed between the curving radiuses sides.

Figure 12:
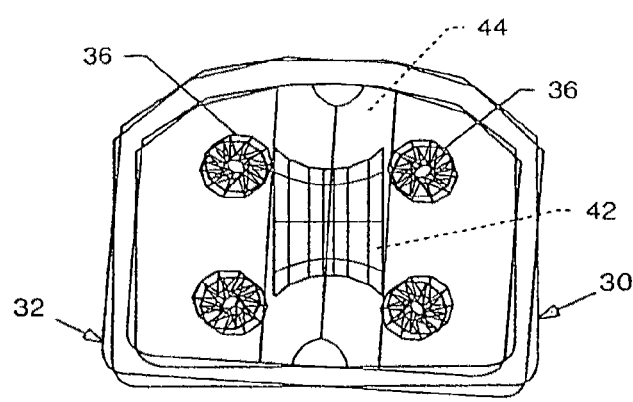
FIG. 12 is a top plan view of the total disc implant of FIG. 7, showing axial rotation.

With this geometry, the part-cylindrical bearing surfaces 42, 44, and the flattened rotational platform defined by offset radii, provide a platform permitting a limited amount of axial rotation and translation. That is, the effect of this special asymmetric articulating geometry with offset radii is to accommodate a substantially natural range of anatomic rotational motion on the order of about plus/minus 5° as viewed in FIG. 12, while at the same time providing a limit to extreme rotation motion and restoring a "neutral" position following a rotation motion. In such rotation, beyond a certain limit imposed by the offset amount, the radiused sides of the curved bearing surface 42 of the top end plate 30 slide along the articulating surface 44 of the bottom end plate 32 effectively distracting the intervertebral disc space. This distraction increases axial loading on the TDI. In turn, the increased axial loading naturally results in a counteracting force tending to resist the distraction, forcing the two vertebral bodies back to the "neutral" position.

Thus, this alternate two piece unique TDI articulation geometry as shown in FIGS. 7-9 functions like the natural disc, by limiting axial rotation while permitting normal anatomic flexion-extension and lateral bending motions. No other features such as positive stops or grooves or additional components such as elastomeric materials are necessary. Another unique advantage of this design is that it does not require an insert, thus avoiding any risk of the insert from being dislodged or otherwise impinging on the spine.

The implant design can be flexible enough to permit a higher range of motion—up to about 20° for flexion-extension and lateral bending for cervical spine disc replacements. The ROM for the proposed lumbar and cervical spines are in accord with those reported by Wilke et al[xvii, xviii] and White and Panjabi[xix].

FIGS. 16-21 illustrate a further alternative preferred form of the TDI of the present invention, based again on principles of maintaining natural spinal anatomy, restoring function by preserving segmental motion, providing immediate implantation stability, withstanding normal spinal loads in a safe and stable manner, and providing relatively rapid and improved osteo-integration between TDI surface and host bone.

Figure 16:
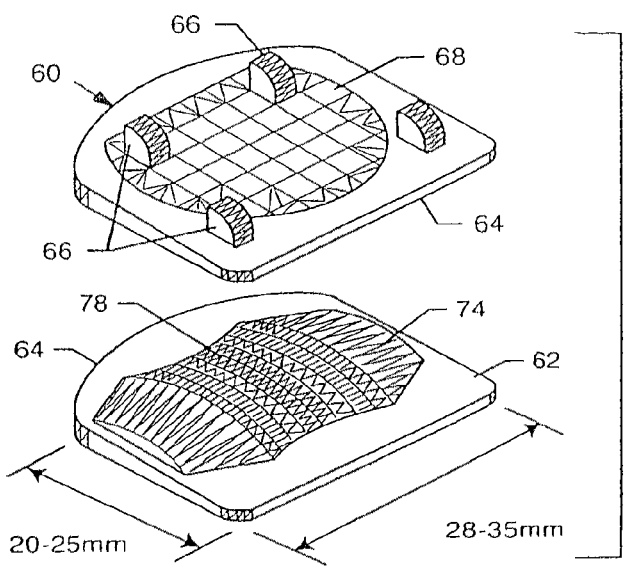
FIG. 16 is an exploded top perspective view showing a total disc implant constructed in accordance with a further alternative preferred form of the present invention.
Figure 17:
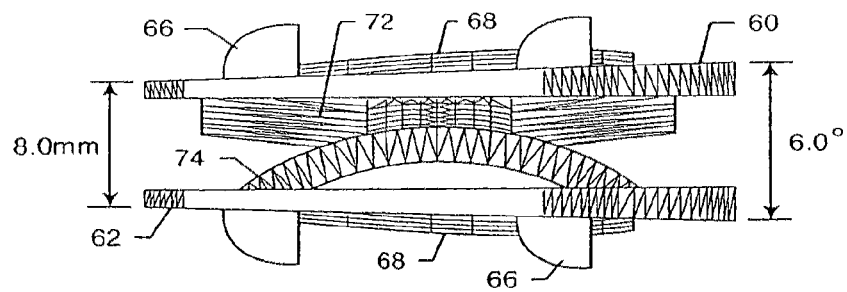
FIG. 17 is a side elevation view of the total disc implant embodiment depicted in FIG. 16.
Figure 18:
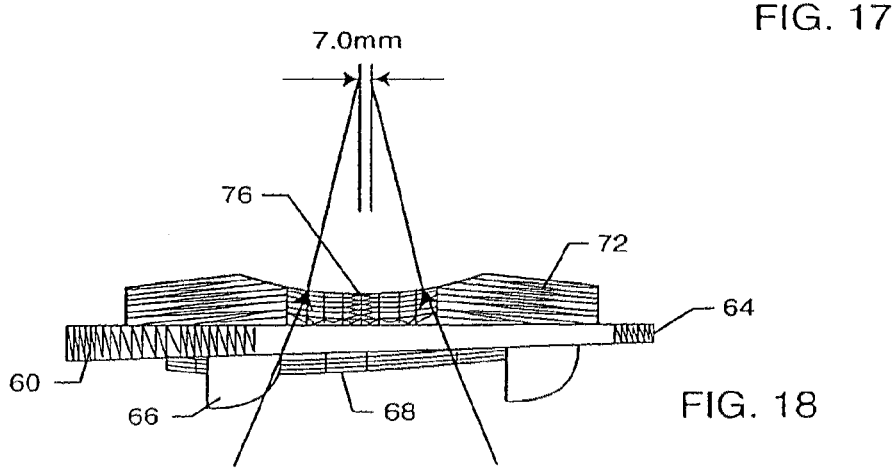
FIG. 18 is an inverted side elevation view of an upper component of the total disc implant embodiment of FIG. 16.

FIGS. 16-17 illustrate an upper end plate 60 and a lower end plate 62 similar to those shown and described in FIGS. 1-9, but respectively including convex or domed upper and lower surfaces for engaging adjacent vertebral bodies having an overall size and shape suitable for implantation into the lumbar spinal region. These domed surfaces are surface-coated with or otherwise define porous bone in-growth surfaces 68 for relatively rapid osteo-integration with porous or cancellous interior structure of prepared adjacent vertebral bodies. A solid rim 64 on each end plate is provided for stable seated engagement with the circumferential or cortical rim of the prepared adjacent vertebral bodies, so that center loading and potential subsidence is substantially eliminated or avoided. Protruding fixation elements 66 such as the illustrative fins are also provided for anchoring the end plates 60, 62, and to provide substantial immediate stability. The illustrative drawings (FIG. 17) show these fins 66 to have a generally curved posterior edge and a generally vertical anterior edge suitable for anterior placement. For anterior-lateral placement, a modified fin shape of generally pyramidal configuration with a triangular base may be used.

As shown and described with respect to the embodiments of FIGS. 1-9, the alternative embodiment of FIGS. 16-21 may incorporate anterior-posterior and medial-lateral dimensions suitable for specific lumbar or cervical spinal body dimensions. The end plates 60, 62 have an anterior to posterior lordotic taper (FIG. 17), similar that shown in FIGS. 2 and 9, for better fit and restoration of the natural spinal curvature.

In addition, the articulating surfaces of the end plates 60, 62 have a unique contour that permits flexion-extension and lateral bending while limiting extreme rotation. In particular, upper end plate 60 includes a depending, part-cylindrical bearing strip 72 which is elongated in the anterior-posterior (sagital) direction, wherein this bearing strip 72 incorporates generally convex opposite end segments separated by a centrally positioned and generally concave segment defining a concave bearing seat 76. By contrast, the lower end plate 62 includes an upwardly projecting, part-cylindrical bearing strip 74 which is elongated along an axis generally orthogonal to the upper bearing strip 72. That is, the part-cylindrical lower bearing strip 74 is elongated in the medial-lateral (coronal) direction, and additionally incorporates generally convex opposite end segments separated by a centrally located and generally concave segment defining a concave bearing seat 78. Accordingly, each bearing strip 72, 74 is shaped with generally convex opposite end segments, preferably to expand or taper with increasing diametric size (FIGS. 16 and 18) from the opposite ends thereof in a direction toward the associated central concave bearing seat 76, 78. As illustrated in inverted configuration in FIG. 18 with respect to the upper bearing seat 76 formed on the upper bearing strip 72, both concave bearing seats 76, 78 which are also oriented on generally orthogonal axes relative to each other are desirably formed on offset radii as previously shown and described relative to FIGS. 1-9, to define upwardly curving opposed sides with a relatively flattened base segment interposed therebetween.

Figure 19:
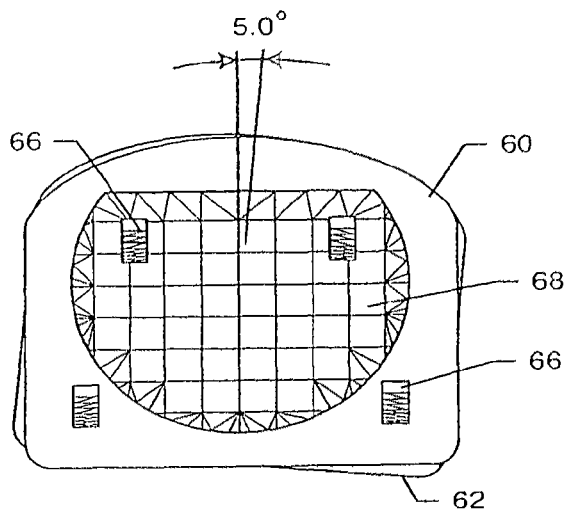
FIG. 19 is a top plan view of the total disc implant embodiment of FIG. 16, showing axial rotation.
Figure 20:
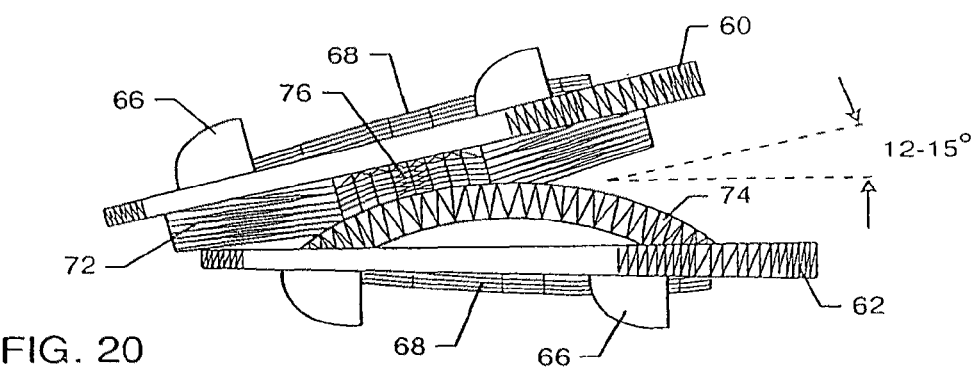
FIG. 20 is an anterior-posterior or sagital sectional view of the total disc implant embodiment of FIG. 16, showing anterior-posterior articulation.
Figure 21:
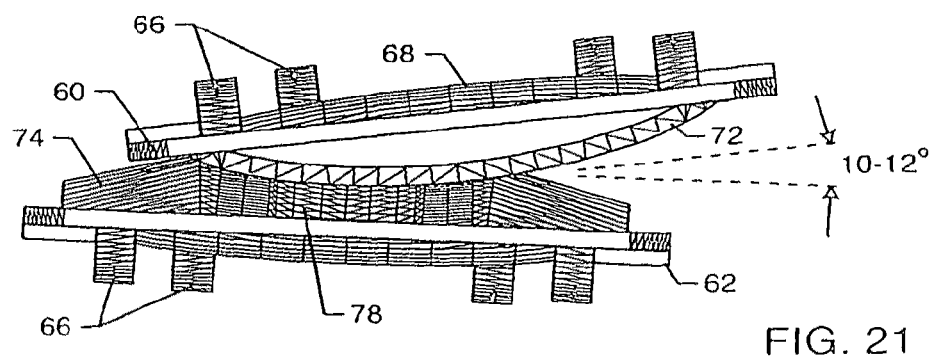
FIG. 21 is a medial-lateral or coronal sectional view of the total disc implant embodiment of FIG. 16, showing medial-lateral articulation.

As viewed in FIGS. 19-21, the above described articulating geometry accommodates limited relative rotation (FIG. 19) within a limited range of about plus/minus 5°, medial-lateral flexion-extension (FIG. 20) within a limited range of up to about 12-15°, and anterior-posterior lateral bending (FIG. 21) within a limited range of up to about 10-12°. The effect of this articulating geometry including the above-described concave surfaces formed on offset radii functions to limit extreme motion and correspondingly to provide an inherent tendency to return to or restore a neutral or substantially centered position between the articulating components. That is, upon extreme rotation, the combination of the offset radii for the concave bearing seats 76, 78 and their engagement on orthogonal axes results in sliding of the upper end plate 60 along the lower end plate 62 for distracting the intervertebral disc space. This distraction increases loading in the cranial-caudal direction on the TDI, which in turn naturally results in a counteracting force tending to resist the distraction, thereby urging the components and the vertebral bodies affixed thereto back toward a neutral position. Thus, the TDI articulation geometry functions like the natural disc, by limiting axial rotation while permitting normal anatomic flexion-extension and lateral bending motions. No other features such as positive stops or grooves or additional components such as elastomeric materials are necessary.

While FIGS. 20 and 21 respectively show the TDI in extreme flexion-extension and extreme lateral bending positions for the illustrative lumbar implant, it is noted the ROM permitted for a cervical implant can be varied typically within a wider range of motion.

In summary then, the proposed TDI is a motion preserving prosthetic disc for replacing a damaged disc, which restores anatomic motion and function, provides immediate and long term stability and virtually eliminates risk from wear particles.

The TDI end plates and/or the insert are constructed from rigid-on-rigid materials, such as by use of a selected ceramic material, or a selected biocompatible metal, or combinations thereof. In the most preferred form, ultra-low wear bearing materials such as enhanced $Si_3N_4$ ceramic is used, as shown and described in copending U.S. Ser. No. 10/171,376, filed Jun. 13, 2002, which is incorporated by reference herein.

In particular, for total hip arthroplasty (THA) implant bearing applications, $Si_3N_4$ cups/$Si_3N_4$ heads have demonstrated high safety and reliability in laboratory hip simulator and mechanical tests, and are cost competitive compared to conventional ceramic-on-ceramic bearings. Compared to presently available state-of-the-art ceramics, such $Si_3N_4$ ceramics have 100% higher fracture toughness than alumina and 50% higher fracture toughness than zirconia, a 50% increase in fracture strength over alumina and no issues with phase transformation or aging like zirconia. They also have very favorable wear performance as determined over a 3 million cycle test. These properties of $Si_3N_4$ allowed THA implants with significantly higher safety and reliability to be manufactured. Wear performance of these bearings indicates that they are better than metal-on-metal bearings by over one order of magnitude, 2 orders of magnitude better than metal-PE and 20 times lower than metal-XPE bearings. These bearing materials are preferred for use in the TDI of the present invention.

Preferred bio-mimetic, bioactive, cancellous structured ceramics (CSC) for use a porous bone in-growth materials and surfaces are shown and described in copending U.S. Ser. No. 10/137,106, filed Apr. 30, 2002, and entitled RADIOLUCENT BONE GRAFT, and U.S. Ser. No. 10/137,108, filed Apr. 30, 2002, and entitled RADIOLUCENT SPINAL FUSION CAGE, both of which are incorporated by reference herein. These CSC ceramics possess [a] high load bearing capability, [b] strong bio-mimetic scaffold necessary for ingrowth and rapid integration with host bone, [c] a bio-active coating comprising of calcium phosphate (Ca—P), which like hydroxy-apatite (HAP) or tri-calcium phosphate (TCP) is similar to bone mineral, a Ca deficient, carbonate containing apatite similar to $Ca_{10}(PO_4)_6(OH)_2$ and capable. of binding to osteo-inductive factors such as autogenous cells, and [d] good imaging characteristics unlike metals. The fabrication processes to make these bio-mimetic structures have been developed.

Figure 13:
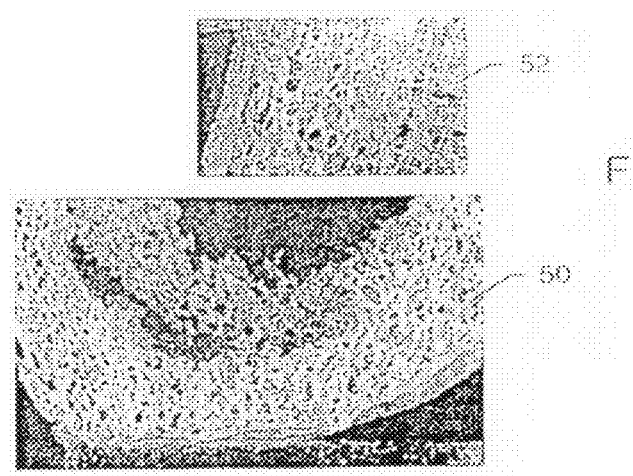
FIG. 13 is a pair of photomicrographs comparing porosity and pore size between a preferred cancellous structured ceramic material for use in forming one or more portions of the total disc implant, with natural trabecular bone structure of a human lumbar vertebral body.

The porosity and pore size of these CSC ceramics can be tailored to allow for [a] optimal ingress of vascularization, [b] ease of carrying/delivering ex-vivo expanded viable hMSCs within the cancellous core, and [c] mechanical property match with bone to allow optimal stress transmission.[xx] The porosity/pore size structure for a load bearing CSC have been selected using previous reports on the optimal structure for grafts by Robey and co-workers.[xxi], Bobyn et al[xxii,xxiii] and Bloebaum et al[xxiv]. The optimal pore size for achieving bone ingrowth ranged between 100 to 530 μm, with up to 55% porosity. The resultant porous structure 50 of the CSC ceramic closely resembles the porous structure 52 of trabecular bone, as viewed in FIG. 13.

These CSCs have been tested in a load bearing sheep condyle defect model.[xxv] using cylindrical CSC plugs (12 mm dia×20 mm long, 70% porous with 500-750 μm pore size) in a sheep condylar defect model (n=6). Extensive in-growth and bone apposition were noted after 12 weeks implantation.

Figure 14:
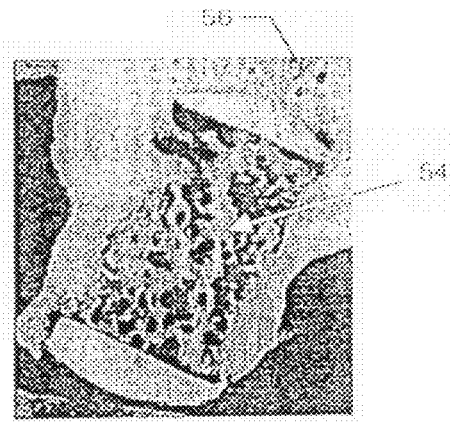
FIG. 14 is a radiograph showing the preferred cancellous structured ceramic material implanted a condylar bone of a sheep.
Figure 15:
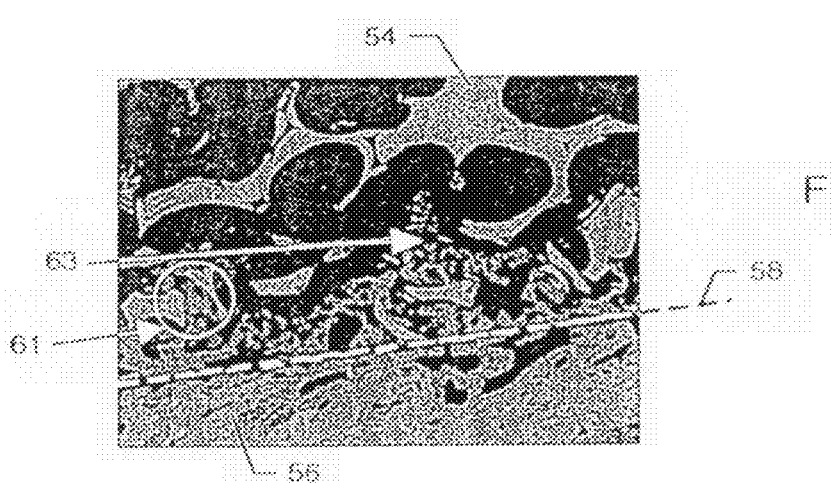
FIG. 15 is a back scattered electron (BSE) microscope image showing new bone ingrowth into the preferred cancellous structured ceramic material, and apposition along the host bone/implant interface.

FIGS. 14 and 15 show a typical section, with a CSC plug 54 implanted with condylar bone 56. The CSC plugs were coated with a uniform amorphous Ca—P coating and pores filled with host bone marrow aspirate. The combination of the Ca—P coating and host osteo-inductive factors resulted in favorable osteoinductive activity. The implant/bone interface is depicted in FIG. 15 by reference numeral 58. Reference numeral 61 refers to a region of bone apposition, and reference numeral 63 indicates bone ingrowth.

Histologic evaluation (Giemsa stain) of thin sections revealed vigorous bone formation both at the implant/host bone interface and within the pores of the scaffold, indicative of the interconnection between pores. At the host bone/CSC implant interface new bone formed at the surface. Complete interconnection of the pores allowed osteoblastic activity to penetrate deeper into the implant and complete vascular penetration was observed in the histology evaluation. In addition to primary and secondary bone, evidence of woven bone was observed. Also, the bone was viable as detected by osteocytes in the lacunae. Little fibrous encapsulation, presence of macrophage or giant cells was detected.

The extent of bone ingrowth in the coated CSC was significantly higher compared to porous coated Ti plugs of similar dimension in a similar model (25% in CSC at 12 weeks. 13% at 12 weeks and 16% at 24 weeks)[xxvi]. Comparison of these preliminary results with in-growth data from the same lab/animal model/implant design/technique indicate that:

CSCs at 12 weeks have 200% and 50% higher in-growth when compared to porous coated Ti plugs at 12 and 24 weeks, respectively.
  New bone forms on the surface in CSCs (similar to HAP/TCP grafts) rather than near the surface (typical for bio-inert materials such as Ti or alumina), and
  Penetration depth of new bone is significantly higher.

The CSC structure will be used to fabricate the porous in-growth surface 18 integrally with the dense bearing surface end plates of the TDI implant as shown in FIG. 1. Excellent short/long term stability and imaging characteristics will be obtained.

The instant TDI is an ideal prosthetic inter-vertebral disc implant. The design maintains intervertebral anatomy. The TDI design restores spinal segmental motion and provides a resistance to extreme rotation of the spine as is desired. The bi-concave insert 20, with its thicker rim 14 will naturally prevent protrusion and resist dislocation. This will minimize risk of pinching nerves or the spinal cord. The ceramic disc insert material offers unprecedented biomechanical safety in carrying and transmitting loads between the vertebrae. The insert is both biocompatible and bio-stable: the disc or any of its wear by-products, are highly unlikely to cause adverse tissue reactions. These attributes if demonstrated, will enable the proposed TDI to leapfrog the present generation of disc implants undergoing clinical testing.

A variety of modifications and improvements in and to the improved disc implant of the present invention will be apparent to persons skilled in the art. For example, it will be recognized and -appreciated that the orientations of the bearing strips 22 and 24 on the upper and lower end plates 10, 12 may be reversed, with a corresponding reversal in the orientation of the bearing seats 26, 28 formed in the insert. Similarly, it will be appreciated and understood that the offset radii concept for forming the bearing seats 26, 28 may also be applied to the bearing strips 22, 24 on the end plates 10, 12. Accordingly, no limitation on the invention is intended by way of the foregoing description and accompanying drawings, except as set forth in the appended claims.

LITERATURE CITED

[i] R A Robinson, "The Results of Anterior Interbody Fusion of the Cervical Spine", J. Bone Joint Surg., 440A: 1569-1586, 1962.

[ii] Callaway G. H, Flynn W., Ranawat C. S., and Sculco T. P., J. Arthroplasty, 10, No.6:855-859, 1995.

[iii] Higuchi F., Shiba N., Inoue A. and Wakabe I., J. Arthroplasty, 10, No.6:851-854, 1995.

[iv] Kirkler S. and Schtzker J., J. Arthroplasty, 10, No.6:860-862, 1995.

[v] Blunn G W, Walker P S, Joshi A, Hardinge K. The dominance of cyclic sliding in producing wear in total knee replacements. Clin Orthop. 1991; 273:253-260.

[vi] Bloebaum R D, Mihalopoulous N L, Jensen J W and Dorr L D, "Postmortem analysis of bone ingrowth into porous acetabular components", JBJS, Vol. 79-A, No. 7, 1013, July 1997.

[vii] Bloebaum R D, Bachus K A, Jensen J W, Scott D F, and Hofmann A A, "Porous coated metal-backed patellar components in total knee replacements", JBJS, Vol. 80-A, no.4, 518, April 1998.

[viii] Bert J M, "Dislocation/subluxation of meniscal bearing elements after New Jersey Low-Contact Stress total knee arthroplasty". Clin Orthop. 1990; 254:211-215.

[ix] Huang R, Girardi F, Cammisa F Jr., and Marnay T, "Long term flexion-extension range of motion of the Prodics-I", Proc. 17$^{th}$ NASS Ann. Mtg., The Spine Journal, 2/93S, 2002.

[x] McAfee P C, Cunningham B W, Devine J G, Williams E, and Yu-Yahiro J, "Classification of heterotopic ossification in artificial disc replacement", Proc. 17$^{th}$ NASS Ann. Mtg., The Spine Journal, 2/94S, 2002.

[xi] Ledet E, Drisio D, Tymeson M, Anderson L, Kallakury B, Sheehan C, and Sachs B, "The Raymedica PDN prosthetic disc nucleus device in the baboon lumbar spine", Proc. 17$^{th}$ NASS Ann. Mtg., The Spine Journal, 2/94S, 2002.

[xii] Wright T M, Hood R W and Burstein A H, "Analysis of Material failures", Orthop. Clin. North Am., 13, 33, (1982).

[xiii] Wroblewski B M, "Wear and loosening of the socket in the Charnley low-friction arthroplasty," Orthop. Clin. North Am., 19, 627, 1988.

[xiv] Wilke H J, Kettler A and Claes L, "Are Sheep a Valid Biomechanical Model for Human Spines?", Spine, 22, 2365-2374, 1997.

[xv] Wilke H J, Krishak S, and Claes L, "Biomechanical Comparison of Calf and Human Spine", J. Orthoped. Res., 14, No. 3, 500, 1996.

[xvi] White A A, and Panjabi M M, "Clinical Biomechanics of the Spine", 2$^{nd}$ ed.,: J B Lipincott, 1990.

[xvii] Wilke H J, Kettler A and Claes L, "Are Sheep a Valid Biomechanical Model for Human Spines?", Spine, 22, 2365-2374, 1997.

[xviii] Wilke H J, Krishak S, and Claes L, "Biomechanical Comparison of Calf and Human Spine", J. Orthoped. Res., 14, No. 3, 500, 1996.

[xix] White A A, and Panjabi M M, "Clinical Biomechanics of the Spine", 2$^{nd}$ ed.,: J B Lipincott, 1990.

[xx] S. D. Boden and J H Schimandle, "The Lumbar Spine", Vol 2, eds. S. W. Wiesel et al, 1996.

[xxi] Mankani M H, Kuznetsov S A, Fowler B, Kingman A, Robey P G, in Biotech., Bioeng, John Wiley & Sons, Inc. 72: 96-107, 2001.

[xxii] Bobyn J D, Pillar R M, Cameron H U and Weatherly G C, Clin. Orthop., 150, pp.263, 1980.
[xxiii] Bobyn J D, et al, Clin. Orthop., 149, pp291, 1980.
[xxiv] Bloebaum R D et at, JBJS, 80,-A, no. 4, pp 518, 1981
[xxv] Lakshminarayanan R., Bireley W., Rao M S, and Khandkar A C, Trans. ORS Mtg., New Orleans, 2003.
[xxvi] Wille B M et al, Trans. ORS Mtg., New Orleans, 2003.

What is claimed is:

1. A spinal disc implant, comprising:
   a first component comprising a first bearing surface and another surface for abutment to a vertebral body; and
   a second component comprising a second bearing surface and another surface for abutment to another vertebral body, one of said first and second bearing surfaces having an at least partially convex shape for articulation with the other of said first and second bearing surfaces having an at least partially concave shape;
   wherein at least one of said first and second bearing surfaces comprises a biocompatible ceramic material comprising doped silicon nitride having a flexural strength greater than about 700 Mega-Pascal (MPa) and a toughness greater than about 7 Mega-Pascal root meter (MPam 0.5),
   wherein at least one of said first and second bearing surfaces has a cross sectional shape defined by laterally spaced-apart, offset radii to include a generally flattened base segment interposed between a pair of curved sides, said bearing surfaces facing each other and extending generally on orthogonal axes relative to each other.

2. The disc implant of claim 1 wherein said doped silicon nitride further includes dopants selected from the group consisting of yttrium oxide, magnesium oxide, strontium oxide, alumina, and combinations thereof.

3. The spinal disc implant of claim 2 wherein said doped silicon nitride comprises $Si_3N_4$ doped with 6 weight % $Y_2O_3$+4 weight % $Al_2O_3$.

4. The spinal disc implant of claim 1 wherein both of said first and second bearing surfaces comprise a ceramic material with a flexural strength greater than about 700Mega-Pascal (MPa) and a toughness greater than about 7 Mega-Pascal root meter $(MPam^{0.5})$.

* * * * *